(12) United States Patent
Schilling et al.

(10) Patent No.: US 8,934,958 B2
(45) Date of Patent: Jan. 13, 2015

(54) MEDICAL DIAGNOSTIC DEVICE AND METHOD FOR DIAGNOSING

(75) Inventors: Meinhard Schilling, Wolfenbuettel (DE); Martin Oehler, Braunschweig (DE)

(73) Assignee: Technische Universität Braunschweig Carolo-Wilhelmina, Braunschweig (DE)

( * ) Notice: Subject to any disclaimer, the term of this patent is extended or adjusted under 35 U.S.C. 154(b) by 599 days.

(21) Appl. No.: 13/266,484

(22) PCT Filed: Apr. 15, 2010

(86) PCT No.: PCT/EP2010/002312
§ 371 (c)(1), (2), (4) Date: Feb. 10, 2012

(87) PCT Pub. No.: WO2010/124794
PCT Pub. Date: Apr. 11, 2010

(65) Prior Publication Data
US 2012/0130225 A1 May 24, 2012

(30) Foreign Application Priority Data
Apr. 30, 2009 (DE) .......... 10 2009 019 242

(51) Int. Cl.
*A61B 5/05* (2006.01)
*A61B 5/0478* (2006.01)
*A61B 5/06* (2006.01)
*A61B 5/00* (2006.01)
*A61B 5/053* (2006.01)
*A61B 5/0402* (2006.01)
*A61B 5/0245* (2006.01)
*A61B 5/0408* (2006.01)

(52) U.S. Cl.
CPC ............. *A61B 5/0478* (2013.01); *A61B 5/065* (2013.01); *A61B 5/0033* (2013.01); *A61B 5/0536* (2013.01); *A61B 5/0402* (2013.01); *A61B 5/0245* (2013.01); *A61B 5/04085* (2013.01); *A61B 5/061* (2013.01); *A61B 2562/0209* (2013.01); *A61B 2562/046* (2013.01)
USPC ............ 600/407; 600/547; 600/508

(58) Field of Classification Search
USPC .................................. 600/407, 547
See application file for complete search history.

(56) References Cited

U.S. PATENT DOCUMENTS 7,505,810 B2 * 3/2009 Harlev et al. ............. 600/509
2005/0107719 A1 * 5/2005 Arad (Abbound) ........ 600/547
2008/0097232 A1 4/2008 Rothenberg (Continued)

FOREIGN PATENT DOCUMENTS

EP 1 800 599 A1 6/2007
WO 2008032234 A1 3/2008

*Primary Examiner* — Jonathan Cwern
(74) *Attorney, Agent, or Firm* — Whitham Curtis Christofferson & Cook, PC (57) ABSTRACT

The invention relates to a medical diagnostic device (1) having at least one sensor matrix (2) for capturing electrical voltage signals at a plurality of locations on the body surface of a person or animal, wherein the diagnostic device (1) is set up for capturing a signal (12) representing the position of the sensor matrix (2) relative to the body of the person or animal, and for determining position information (14) about the position of the sensor matrix (2) relative to the body, localized image information (13) is determined from the voltage signals, and the localized image information (13) is associated with the position information (14).

12 Claims, 5 Drawing Sheets

(56) References Cited

U.S. PATENT DOCUMENTS

| | | | |
|---|---|---|---|
| 2008/0167553 A1* | 7/2008 | Paltieli et al. | 600/437 |
| 2008/0319331 A1* | 12/2008 | Zizzo et al. | 600/511 |
| 2009/0234242 A1 | 9/2009 | Svojanovsky | |
| 2010/0097374 A1* | 4/2010 | Fan et al. | 345/420 |

* cited by examiner

MEDICAL DIAGNOSTIC DEVICE AND METHOD FOR DIAGNOSING

CROSS-REFERENCE TO RELATED APPLICATIONS

This application claims the benefit of PCT Application No. PCT/EP2010/002312, filed Apr. 15, 2010, which is based on German Application No. 10 2009 019 242.5 filed Apr. 30, 2009.

FIELD OF THE INVENTION

The invention relates to a medical diagnostic device as per the preamble of patent claim 1 and a corresponding method for medical diagnostics.

BACKGROUND

DE 10 2004 063 249 A1 has disclosed a sensor system for capacitive measurement of electromagnetic signals with a biological origin. The capacitive electrodes explained therein make it possible to record e.g. an electrocardiogram (EKG) or an electroencephalogram (EEG) in a novel fashion. The electrodes presented therein can be manufactured in a cost-effective fashion, and so a corresponding medical diagnostic device can be equipped with a plurality of such electrodes as sensors. By way of example, the plurality of electrodes can be arranged in a matrix-like fashion and thus form a sensor matrix. This makes it possible, in a simple fashion, to undertake the measurements at different points on the body that are required during the generation of EKGs. In particular, this dispenses with the need for attaching a multiplicity of individual electrodes to the body, as known from conventional EKG systems with adhesive or suction electrodes. The novel capacitive electrodes more particularly also permit EKGs to be recorded through textiles, and so there is no need to undress a patient.

SUMMARY

The invention is based on the object of specifying a medical diagnostic device with such a sensor matrix, which allows a larger field of use compared to known EKG systems and improved diagnostic options. It is moreover an object of the invention to specify a diagnostic method suitable for this.

This object is achieved by the invention as per claims 1 and 12. The dependent claims specify advantageous developments of the invention.

The inventors have identified that a medical diagnostic device with a sensor matrix, i.e. a plurality of sensors distributed in a particular fashion, advantageously also allows spatially resolved image representations, e.g. in the form of two-dimensional image information, in addition to the known conventional representation of EKG measurements in the form of time diagrams. According to the invention, the image information obtained from the voltage signals captured by means of the sensor matrix can advantageously be supplemented by position information. The position information specifies the position of the sensor matrix relative to the body. This enables simple and quick identification of associated body regions and hence simplifies and accelerates the evaluation by a medical practitioner and the preparation of the medical diagnosis. Moreover, the reproducibility of the measurements is improved because the position information allows quick orientation in respect of the image contents of the person evaluating the image information.

In particular, it is possible to generate an image of the anatomy of the examined body at the same time as generating the functional imaging, i.e. the image information generated by the sensor matrix. This allows the image information to be displayed relative to the position of the anatomical situation in the examined body part. The invention can advantageously be used to orient the functional image on the anatomical image and to display the functional image aligned to the anatomy, independently of the location and position of the diagnostic device. Thus, for example, it is also possible to display the position of the lungs or the ribs as additional image information in addition to a two-dimensionally displayed and hence spatially resolved EKG. As a result, the position of the diagnostic device relative to the thorax is unimportant because the spatially resolved EKG no longer needs to be displayed relative to the sensor matrix but rather can be automatically displayed relative to the anatomy of the examined body.

As per an advantageous development of the invention, the diagnostic device is designed to capture an electrocardiogram or an electroencephalogram. As a result the diagnostic device according to the invention can be used particularly universally. In the embodiment for capturing an electroencephalogram, the sensor matrix is attached to a unit, e.g. a helmet, to be fixed to the head of the human or animal to be examined.

In particular, the sensor matrix can advantageously be positioned relative to the body of the human or animal according to the principle of impedance tomography using electric and/or magnetic signals.

As per an advantageous development of the invention, the diagnostic device is designed to capture a surrounding electromagnetic field and to evaluate the captured field for determining the position of the sensor matrix relative to the body of the human or animal. In principle, any electric, magnetic or electromagnetic field that is present in the surroundings in any case, e.g. interference radiation from consumer goods, comes into question as surrounding field. Any external field can be captured herein, e.g. the 50 hertz field from the 220 volt AC voltage supply.

In particular, the radio signal emitted by radio transmitters can be used as surrounding field because it has relatively high field strength and is emitted from a relatively large distance in comparison with the size of the diagnostic device. As a result of the large distance, the field captured for determining the position is substantially invariant with respect to minor changes in the position of the body to be examined or the diagnostic device. As a result, the position of the sensor matrix relative to the body of the human or animal can be determined in a relatively well reproducible and precise fashion by using such a surrounding field.

Advantageously the same sensors in the sensor matrix are used to capture the signal that represents the position of the sensor matrix relative to the body of the human or animal and to capture the electric voltage signals at the body surface of the human or animal. Thus, it is advantageously possible to make do without additional sensors, as a result of which the invention can be implemented practically in a relatively cost-effective and efficient fashion. In particular, there is no need either for additional evaluation electronics for further sensor signals.

However, in an advantageous embodiment the diagnostic device according to the invention can also have a further sensor for capturing the signal representing the position of the sensor matrix relative to the body. The further sensor can be designed to capture a magnetic field, an electric field, an electromagnetic field, a sonic field or X-ray radiation. A person skilled in the art accordingly designs the required functional principle of the sensor. By way of example, the further sensor can be arranged at a defined position in the region of the sensor matrix on the diagnostic device, or, in the case of a plurality of further sensors, these can be arranged at various defined positions in the aforementioned region. An advantage of using a separate further sensor for capturing the position signal lies in the fact that use can be made of different functional principles for the sensor. Thus, for example, the sensor matrix can be assembled from capacitive sensors as per DE 10 2004 063 249 A1. The further sensor may be e.g. a sound sensor, e.g. a microphone. As a result, different physical variables can be utilized as position signal. A combination of different sensor principles for evaluating different position signals is also advantageous.

As per one advantageous development of the invention, provision is made for a signal coupler for coupling a position signal into the body of the human or animal. The signal coupler can be embodied connected to the diagnostic device or it can be embodied as a separate device. Advantageously the signal coupler should be arranged at a defined position with respect to the body to be examined. The coupled-in signal is distributed in the body and is in turn captured and evaluated by the diagnostic device.

Thus, for example, for examining humans, it is possible that the signal coupler should always be arranged below the left armpit. This affords the possibility of securely and well-reproducibly assigning the position of the image information in a defined fashion, even in the case of non-uniform or non-evaluable surrounding fields. A separate signal coupler for coupling-in the position signal is furthermore advantageous in that it is possible to couple in a specific desired physical signal, such as e.g. an ultrasound signal or an X-ray signal. Hence, it is also possible to use physical signal types for the position signal that, in general, are unsuitable or not available as surrounding fields.

The signal coupler is advantageously designed to couple in a magnetic field, an electric field, an electromagnetic field, a sonic field or X-ray radiation. If embodied as a sound source, the signal coupler can for example be embodied as an ultrasound source. By way of example, the ultrasound source can advantageously be integrated into the diagnostic device and arranged in the region of the sensor matrix. Advantageously, any other type of sound, like e.g. music signals, can be used for coupling into the body in addition to ultrasound.

Advantageously, the further sensor for capturing the signal representing the position of the sensor matrix relative to the body is designed for the same physical signal type, e.g. ultrasound or X-ray radiation, as the signal coupler.

As per an advantageous development of the invention, provision is made for a display apparatus. The diagnostic device is designed to correlate a plurality of individual items of image information, determined by the sensor matrix, to one another on the basis of their position information. Such a correlation between a plurality of items of image information can, for example, increase the size of the image representation and/or the resolution of the display. In order to increase the image size, a plurality of items of image information are advantageously displayed side-by-side. In the process, the items of image information are combined next to one another and above one another such that an increased image-representation region is generated. In order to increase the resolution of the display, a plurality of items of image information are advantageously displayed superposed on one another. Here, the superposition can be undertaken such that e.g. the items of image information are superposed with a small offset with respect to one another, which offset is of the order of a fraction of an item of pixel information of an originally captured item of image information. It is possible to multiply the resolution of the display as a result of a corresponding superposition of a relatively large number of items of image information and a small shift in both coordinate directions.

In addition to single-image information, image information is also understood to mean a sequence of images within the meaning of a film. Since the diagnostic device can advantageously be utilized for recording an EKG, an EKG display over time is once again possible by playing back, successively in time like a film, image information spatially resolved according to the invention; this EKG display can be compared to EKG time profiles from conventional systems. Advantageously the diagnostic device is designed to playback the film at a speed that can be selected by the user. In particular, playback in a temporally stretched representation (slow motion) is advantageous for making a diagnosis on the basis of the image information.

In an advantageous embodiment of the invention, the medical diagnostic device is designed as a device that can be carried by a human and hence it is, as it were, a portable device. Hence the device can advantageously be taken along in mobile medical operations, e.g. in an ambulance or by paramedics.

The invention makes possible an advantageous method for medical diagnosis, comprising the steps of:
  capturing electric voltage signals at a plurality of points on the body surface of a human or animal by means of a sensor matrix,
  capturing a signal representing the position of the sensor matrix relative to the body of the human or animal,
  determining position information in respect of the position of the sensor matrix relative to the body,
  determining spatially resolved image information from the voltage signals and
  associating the position information with the image information.

The method in particular permits a use of the previously explained functions of the diagnostic device.

BRIEF DESCRIPTION OF THE DRAWINGS

In the following text, the invention will be explained in more detail on the basis of exemplary embodiments using drawings.
In Detail

DETAILED DESCRIPTION

In the figures, the same reference signs are used for elements that correspond to one another.

Figure 1:
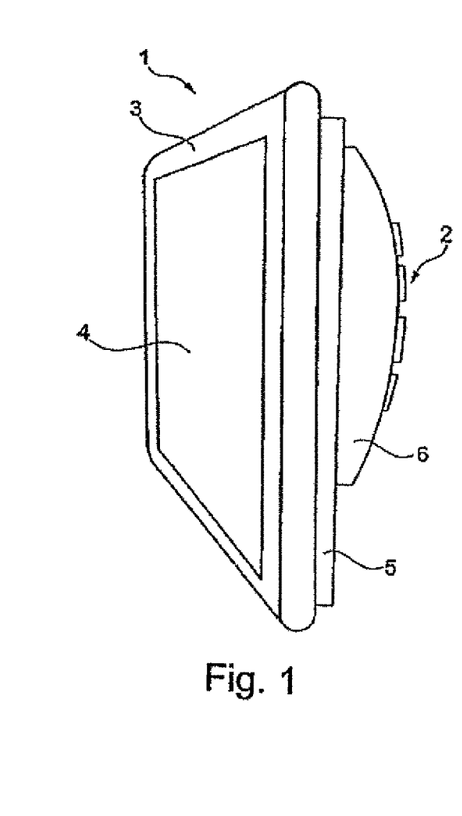
FIGS. 1 to 3 show various views of a diagnostic device and
  FIGS. 4 and 5 show further embodiments of the diagnostic device and
  FIG. 6 shows an EKG diagram and
  FIG. 7 shows a multiple EKG diagram and
  FIG. 8 shows a two-dimensionally spatially resolved EKG diagram.
Figure 2:
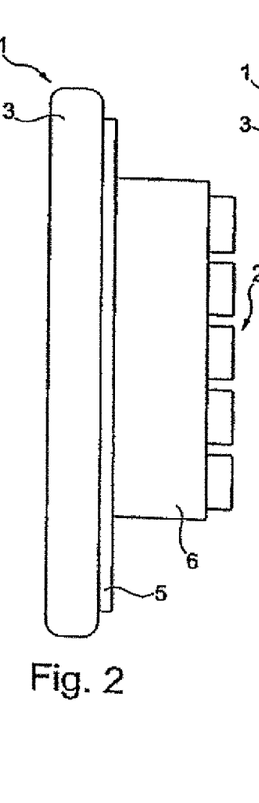
Figure 3:
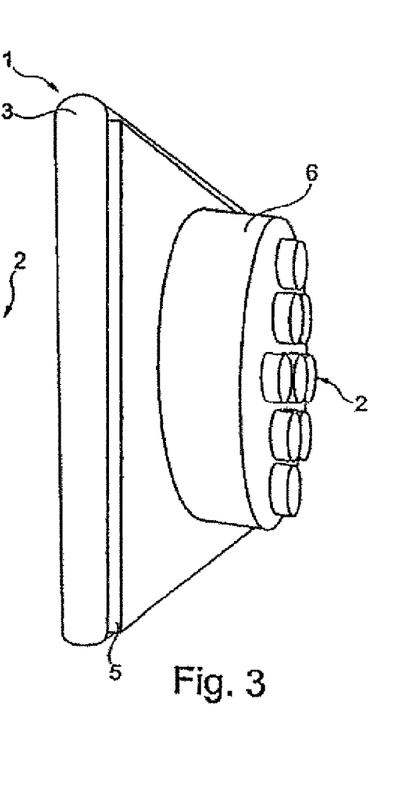

FIG. 1 illustrates the diagnostic device according to the invention in a perspective illustration from the front left. FIG. 2 shows a lateral view and FIG. 3 shows the diagnostic device in a perspective illustration from the back left. The diagnostic device 1 has a computer apparatus 3 with a display apparatus 4. By way of example, the computer apparatus 3 can be embodied as a tablet PC. Advantageously, use can also be made of a laptop or notebook. This makes the diagnostic device relatively easy to handle and easily transportable. A housing 6 is arranged over an assembly plate 5 on the rear side of the computer apparatus 3. Sensors, which are arranged according to a predetermined regular pattern and form a sensor matrix 2, project out of a rear side of the housing 6. By way of example, the sensors are designed as capacitive sensors as per DE 10 2004 063 249 A1. In an advantageous embodiment the sensors are arranged resiliently in the housing 6 such that they yield when placed onto the body of a human or animal and are able to match the body shape to a certain extent. On their side facing the body to be examined, the sensors are respectively insulated, which prevents galvanic contact with the body surface.

Furthermore, provision is made in the housing 6 for an evaluation apparatus in the form of an electronic circuit, which captures and processes the voltage signals generated by the sensor matrix and emits said signals to the computer apparatus 3 via an interface. The computer apparatus 3 advantageously has software for recording, storing and displaying this data on the display apparatus 4.

Figure 4:
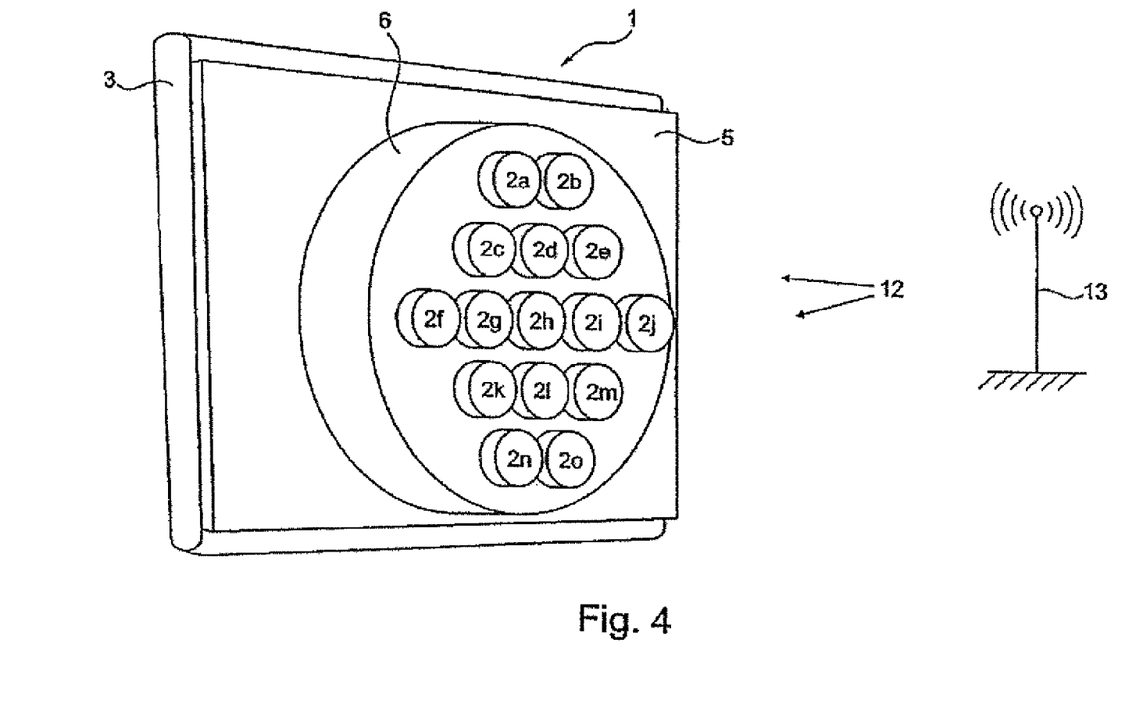

FIG. 4 illustrates a further embodiment of the diagnostic device 1, in which the sensors of the sensor matrix 2 are numbered by reference signs 2a to 2o. The sensors 2a to 20 are provided additionally for capturing a surrounding field 12. By way of example, interference radiation arising in the surroundings or a radio signal from a radio transmitter 13 comes into question as surrounding field 12. The surrounding field 12 is likewise captured and evaluated by the evaluation apparatus arranged in the housing 6 and transmitted to the computer apparatus 3 as position information. The computer apparatus 3 associates the position information with the image information when the image information is generated from the voltage signals from the sensor matrix 2. This captures the relative position of the sensor matrix 2 with respect to the body of the human or animal.

Figure 5:
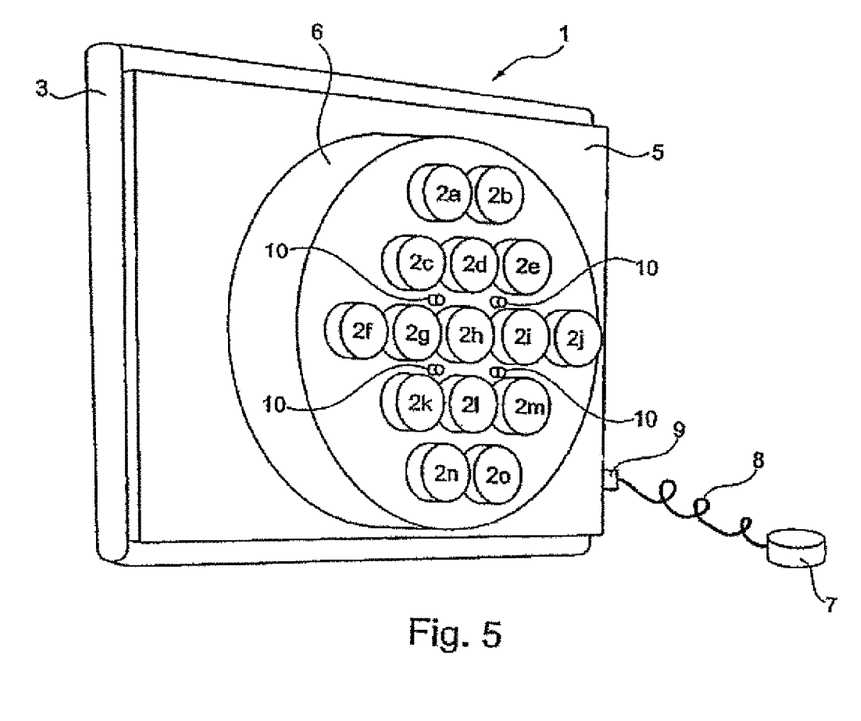

FIG. 5 illustrates a further embodiment of the diagnostic device 1. The diagnostic device 1 is connected to a signal coupler 7 via a connector plug 9 and a line 8. The signal coupler 7 serves for coupling a position signal into the body of the human or animal. The signal coupler is attached to a defined position on the body. This position is predefined such that it is known to the diagnostic device 1. The diagnostic device 1 captures the coupled-in signals, e.g. once again via the sensor matrix 2, and from this determines the position information.

Moreover, the diagnostic device 1 is provided with further sensors 10 that are arranged on the rear side of the housing 6 in the region of the sensor matrix 2. The further sensors 10 are provided as an alternative to capturing the signal representing the position of the sensor matrix relative to the body, e.g. the signal coupled into the body by the signal coupler 7. The further sensors 10 are e.g. embodied as coils that serve for capturing a magnetic field.

Figure 6:
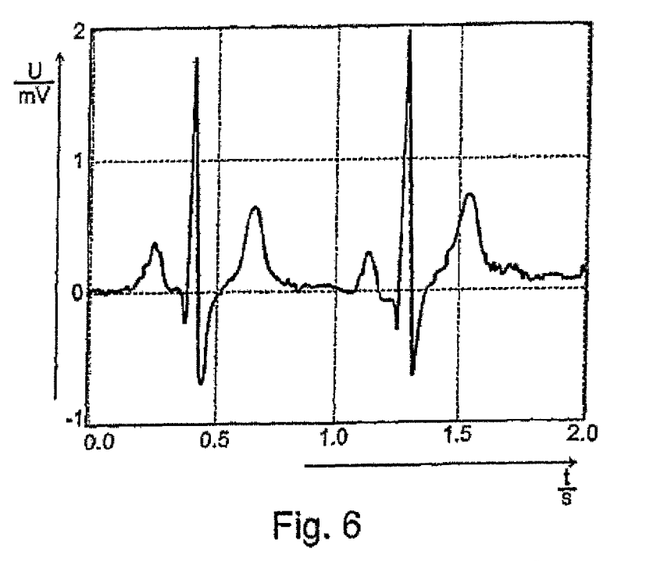

FIG. 6 illustrates a conventional EKG signal, as recorded by known EKG systems. A profile of a voltage U, measured in mV (millivolt), is reproduced against time t, measured in seconds s.

Figure 7:
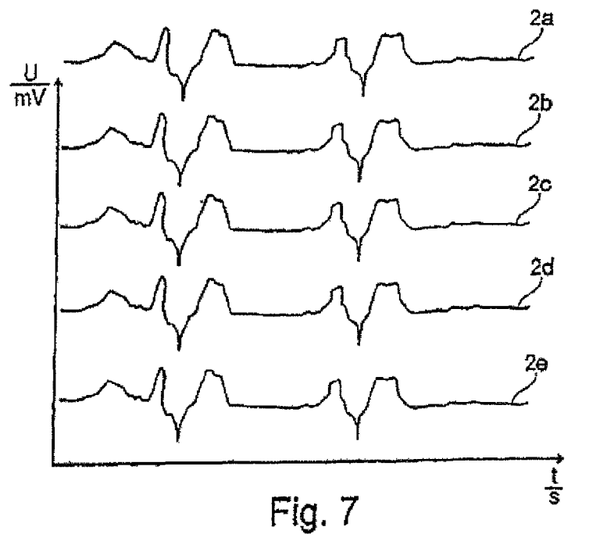

FIG. 7 shows a multiplicity of EKG signals in one diagram. The diagnostic device according to the invention allows the display of a multiplicity of EKG signals as a result of its plurality of sensors in the sensor matrix 2. FIG. 7 reproduces, merely in an exemplary fashion, a diagram of voltage profiles over time from the voltage signals measured by the sensors 2a, 2b, 2c, 2d and 2e.

Figure 8:
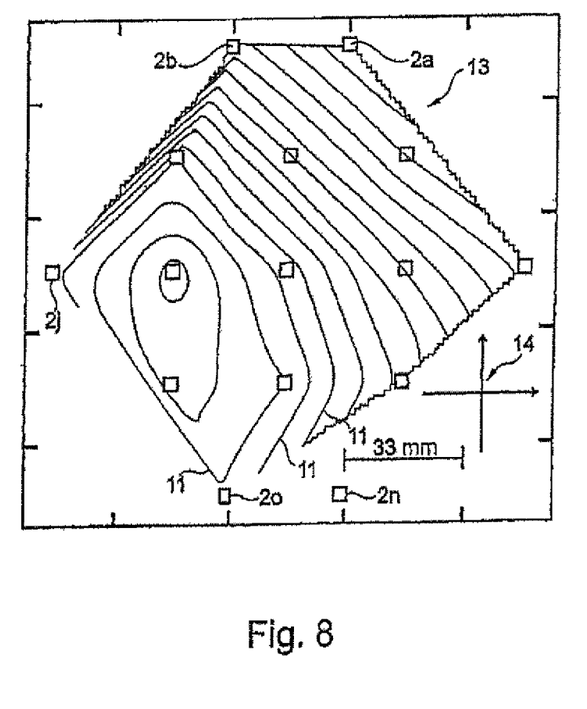

FIG. 8 shows a spatially resolved display of the voltage signals recorded by the sensors 2a to 2o, as may be reproduced on the display apparatus 4. The voltage signals are illustrated spatially resolved in two dimensions and respectively associated with the real positions of the sensors 2a to 20 on the rear side of the housing 6. The positions of the sensors 2a to 2o are reproduced by quadratic symbols in the diagram. For reasons of clarity, only the symbols associated with sensors 2a, 2b, 2j, 2n and 20 have been provided with corresponding reference signs. The computer apparatus 3 calculates equipotential lines 11 from the voltage signals from the sensors 2a to 2o. Depending on the magnitude of the potential, i.e. the measured voltage, the areas between the equipotential lines 11 are reproduced using different grayscale values or different colors.

In FIG. 8, the image information 13 is reproduced, in an exemplary fashion, together with position information 14 illustrated in the style of a coordinate system. The position information 14 makes it possible for the user of the diagnostic device to orient himself easily with respect to the position of the diagnostic device relative to the body. If the diagnostic device is displaced with respect to the body, the position information 14 in the illustration as per FIG. 8 or on the display apparatus 4 is displaced accordingly.

The invention claimed is:

1. A medical diagnostic device for imaging a body of a human or animal, comprising:
    at least one sensor matrix configured to capture electric voltage signals at a plurality of points on an outer body surface of the human or animal, wherein one or more sensors of the at least one sensor matrix are configured to capture a separate signal representing a position of the at least one sensor matrix relative to the body of the human or animal;
    an evaluation apparatus configured to generate a functional image from the electric voltage signals and determine anatomical position information concerning the position of the at least one sensor matrix relative to the body from the separate signal; and
    a display apparatus that displays the functional image oriented with respect to anatomy of the body using the anatomical position information.

2. The medical diagnostic device as claimed in claim 1, wherein the electric voltage signals for which the at least one sensor matrix is configured to capture includes an electrocardiogram (EKG) signal or an electroencephalogram (EEG) signal.

3. The medical diagnostic device as claimed in claim 1, wherein the at least one sensor matrix is configured to capture a surrounding electromagnetic field, and the evaluation apparatus is configured to evaluate the captured electromagnetic field for use in determining the position of the at least one sensor matrix relative to the body of the human or animal.

4. The medical diagnostic device as claimed in claim 1, wherein the one or more sensors configured to capture the separate signal capture a magnetic field, an electric field, an electromagnetic field, a sonic field or X-ray radiation.

5. The medical diagnostic device as claimed in claim 1, further comprising a signal coupler for coupling a position signal into the body of the human or animal.

6. The medical diagnostic device as claimed in claim 5, wherein the signal coupler is configured to couple in a magnetic field, an electric field, an electromagnetic field, a sonic field or X-ray radiation.

7. The medical diagnostic device as claimed in claim 1, wherein the at least one sensor matrix includes capacitive sensors.

8. The medical diagnostic device as claimed in claim 1, wherein the diagnostic device is configured to correlate a plurality of individual items of functional image information generated by the evaluation apparatus to one another on a basis of their anatomical position information.

9. The medical diagnostic device as claimed in claim 8, wherein the plurality of items of functional image information are displayed side-by-side on the display apparatus.

10. The medical diagnostic device as claimed in claim 8, wherein the plurality of items of functional image information are displayed superposed on one another on the display apparatus in order to increase a resolution of a displayed image.

11. The medical diagnostic device as claimed in claim 1, wherein the medical diagnostic device is configured to be portable and carriable by a human for mobile use.

12. A method for imaging a body of a human or animal, comprising the steps of:
- capturing electric voltage signals at a plurality of points on an outer body surface of a human or animal with at least one sensor matrix,
- capturing a separate signal representing a position of the at least one sensor matrix relative to the body of the human or animal with one or more sensors in the at least one sensor matrix,
- determining from the separate signal anatomical position information concerning the position of the at least one sensor matrix relative to the body with an evaluation apparatus,
- generating a functional image from the electric voltage signals with the evaluation apparatus, and
- displaying the functional image oriented with respect to anatomy of the body using the anatomical position information with a display apparatus.

* * * * *